United States Patent [19]

Heinsohn et al.

[11] Patent Number: 5,139,943
[45] Date of Patent: Aug. 18, 1992

[54] PROCESSES FOR THE RECOVERY OF MICROBIALLY PRODUCED CHYMOSIN

[75] Inventors: Henry G. Heinsohn, Pacifica; Jeffrey D. Lorch; Kirk J. Hayenga, both of San Mateo; Raymond E. Arnold, San Francisco, all of Calif.

[73] Assignee: Genencor International, Inc., South San Francisco, Calif.

[21] Appl. No.: 537,464

[22] Filed: Jun. 13, 1990

Related U.S. Application Data

[63] Continuation-in-part of Ser. No. 365,937, Jun. 13, 1989.

[51] Int. Cl.$^5$ .............................................. C12N 9/64
[52] U.S. Cl. .................................... 435/226; 435/815; 435/816; 426/36; 426/42
[58] Field of Search .................... 435/226, 815, 816; 426/36, 42

[56] References Cited

U.S. PATENT DOCUMENTS

| | | | |
|---|---|---|---|
| 2,339,931 | 1/1944 | Keil | 195/68 |
| 3,281,332 | 10/1966 | Munns et al. | 195/66 |
| 3,357,894 | 12/1967 | Uriel et al. | 195/66 |
| 3,415,804 | 12/1968 | Polson | 260/112 |
| 3,816,260 | 6/1974 | Sugiyama | 195/62 |
| 3,834,990 | 9/1974 | Werle et al. | 195/68 |
| 3,890,198 | 6/1975 | Kobayashi et al. | 195/66 R |
| 3,917,510 | 11/1975 | Kitamura et al. | 195/2 |
| 4,016,039 | 4/1977 | Schreiber | 195/66 R |
| 4,144,130 | 3/1979 | Kula et al. | 195/66 R |
| 4,250,084 | 2/1981 | Trainin | 260/112 R |
| 4,299,858 | 11/1981 | Aubert et al. | 426/656 |
| 4,305,871 | 12/1981 | Shanbrom | 260/112 B |
| 4,343,735 | 8/1982 | Menge et al. | 260/112 R |
| 4,439,358 | 3/1984 | Coan et al. | 260/112 B |
| 4,461,833 | 7/1984 | Gordon | 435/183 |
| 4,470,969 | 9/1984 | Pancham et al. | 424/101 |
| 4,508,825 | 4/1985 | Kim et al. | 435/201 |
| 4,530,903 | 7/1985 | Leuchtenberger et al. | 435/130 |
| 4,590,161 | 5/1986 | Kula et al. | 435/104 |
| 4,591,563 | 5/1986 | Paul et al. | 435/193 |
| 4,601,986 | 7/1986 | Wegner et al. | 435/255 |
| 4,666,843 | 5/1987 | Subramanian | 435/226 |
| 4,666,847 | 5/1987 | Alford et al. | 435/253 |
| 4,683,294 | 7/1987 | Van Wijnendaele et al. | 530/371 |
| 4,684,723 | 8/1987 | Dove et al. | 530/351 |
| 4,697,003 | 9/1987 | Coan | 530/380 |
| 4,721,673 | 1/1988 | Uren et al. | 435/183 |
| 4,728,613 | 3/1988 | Brewer et al. | 435/222 |
| 4,743,551 | 5/1988 | Subramanian | 435/226 |
| 4,745,063 | 5/1988 | Birschbach | 435/226 |

OTHER PUBLICATIONS

Andersson et al., *Enzyme and Microb. Technol.*, vol. 7, pp. 333-338 (1985).
Marston et al., *Biotechnology*, pp. 800-804 (1984).
Kula et al. "Purification of Enzymes of Liquid-Liquid Extraction" pp. 73-117.
Engstrom and Wong, "Milk Clotting Enzymes and Cheese Chemistry", in *Fundamentals of Dairy Chemistry*, 2d ed., ed. Webb et al., pp. 674-679 (1983).
Foltmann, "General and Molecular Aspects of Rennets" pp. 33-61.

*Primary Examiner*—Charles L. Patterson, Jr.
*Attorney, Agent, or Firm*—Burns, Doane, Swecker & Mathis

[57] ABSTRACT

Disclosed are methods for the recovery of microbially produced chymosin. In particular, disclosed are methods for the recovery of chymosin from the fermentation beer arising from culturing microorganisms which have been engineered so as to produce chymosin. Also disclosed are methods for the selective recovery and subsequent purification of microbially produced chymosin.

29 Claims, No Drawings

PROCESSES FOR THE RECOVERY OF MICROBIALLY PRODUCED CHYMOSIN

CROSS-REFERENCE TO RELATED APPLICATIONS

This application is a continuation-in-part of U.S. Ser. No. 07/365,937, filed on Jun. 13, 1989, titled "Processes for Recovery and Purification of Chymosin", which is incorporated herein by reference in its entirety.

BACKGROUND OF THE INVENTION

1. Field of the Invention

This invention relates to the recovery of microbially produced chymosin. In particular, this invention is directed to methods for the recovery of chymosin from the fermentation beer arising from culturing microorganisms which have been engineered so as to produce chymosin. This invention further relates to methods for the selective recovery and subsequent purification of microbially produced chymosin.

2. State of the Art

Chymosin is a known enzyme which is particularly useful in the preparation of cheese. Until recently, almost all chymosin employed commercially was recovered from the fourth stomach of a calf, although recovery of chymosin from the stomachs of other mammals, such as lamb, goats, etc. has also been heretofore known. However, due to the recent decrease in calf production, such natural sources of chymosin have declined which, in turn, has provided impetus to microbial generation of chymosin. Thus, recent patents and patent applications have disclosed that chymosin can be produced by the fermentation of genetically engineered microorganisms. For example, the production of chymosin by fermentation of filamentous fungi which have been genetically modified to express and secrete chymosin, is disclosed in U.S. patent application of Lawlis et al., Ser. No. 07/163,219, filed Feb. 26, 1988, which is incorporated in its entirety herein by reference. Likewise, U.S. Pat. No. , 4,666,847, which issued on May 19, 1987 and which is incorporated herein by reference in its entirety, discloses the production of chymosin be fermentation of E. coli (a bacteria) which have been genetically modified to express and secrete chymosin as well as the production of chymosin be fermentation of Saccharomyces cerevisiae (a yeast) which has been genetically modified to express and secrete chymosin.

Because the microbial production of chymosin results in the expression of enzymes in addition to chymosin, recovery and purification of chymosin from the fermentation beer has been an ongoing problem. For example, when chymosin is produced in the manner of U.S. Ser. No. 07/163,219, enzymes such as alpha-amylase, acid phosphates, leu amino peptidase, etc., are co-produced during such fermentation. The presence of such additional enzymes in the fermentation beer imparts an additional level of difficulty in the recovery and purification of chymosin from such beers.

While numerous methods are disclosed for isolating enzymes from a fermentation beer, none of the references which Applicants are aware of specifically disclose that chymosin can both be recovered in extremely high quantities, i.e., partition coefficients (K)>85, and selectively from a fermentation beer containing enzymes in addition to chymosin.

For example, U.S. Pat. No. 4,144,130 describes the use of (1) a mixture of a high molecular weight unsubstituted or substituted polyalcohol, polyether, polyvinylpyrrolidone or polysaccharide and an inorganic salt, (2) a mixture of at least two of the above high molecular weight polymers to recover intracellular enzymes from an aqueous solution into which they have been released from the cells. When a mixture of polyethylene glycol and an inorganic salt is used, the desired intracellular enzyme goes into the top polyethylene glycol layer while the cell debris and other fermentation products go into the lower salt-containing layer. This reference discloses that the partition coefficients for various enzymes recovered in the glycol layer was about 0.3 when a normal cell mass was treated, which could be increased to about 3 when frozen cells were mixed with water and disintegrated to release their enzymes. However, this reference does not teach or suggest the selective recovery of a single enzyme, let alone chymosin from a fermentation beer containing more than one enzyme.

Similarly, U.S. Pat. No. 4,728,613, discloses a process for the recovery of extracellularly produced enzymes, such as protease, amylase and microbial rennet, from whole fermentation beer by using an inorganic salt in combination with a polymer selected from the group consisting of polyethylene glycol, an amine derivative of polyethylene glycol, a carboxylate derivative of polyethylene glycol, polypropylene glycol, an amine derivative of polypropylene glycol, a carboxylate derivative of polypropylene glycol, poly(ethylene glycol) ester, polythyleneimine, trimethylamino-polyethylene glycol, polyvinyl alcohol, polyvinylpyrrolidone and mixtures thereof. While the examples of this reference disclose achieving partition coefficients of up to about 80 for such extracellular enzymes, this reference does not specifically disclose the recovery of chymosin from a polyethylene glycol/salt mixture nor does it disclose the selective recovery of chymosin from a fermentation beer containing more than one enzyme.

Likewise, Kula et al., "Purification of Enzymes by Liquid-Liquid Extraction", describes numerous methods for the purification of enzymes by liquid-liquid extraction. Among numerous methods disclosed, Kula et al. disclose that the addition of a polyethylene glycol/inorganic salt mixture to an aqueous solution containing the enzyme will form a two phase system wherein the polyethylene glycol phase will contain the enzyme. Kula et al. further disclose at page 111 that the phase forming polymer (polyethylene glycol) can be removed from the enzyme by adsorption of the enzyme onto ion exchangers; washing away of the phase forming polymer; and the subsequent recovery of the enzyme. However, this reference does not specifically disclose the recovery of chymosin using a polyethylene glycol/salt mixture nor does it disclose the selective recovery of chymosin from a fermentation beer containing more than one enzyme.

On the other hand, U.S. Pat. No. 4,508,825 discloses that extracellular protease and amylase co-produced during the fermentation of a microorganism capable of producing them are separated by the addition of polyethylene glycol and a cationic epihalohydrin/polyamine copolymer or dextran polymer to the fermentation medium and allowing the polymers to phase separate to form a protease rich phase and an amylase rich phase.

Also, U.S. Pat. No. 4,591,563, discloses a process for the simultaneous purification and concentration of the dextran-sucrase enzyme from the culture medium on sucrose. In particular, the disclosed method involves the addition of a polyether such as polyethylene glycol so as to form two phases; the first a heavy dextran-rich phase that contains the concentrated and purified dextran-sucrase enzyme, and the second a lighter polyether-rich phase that contains contaminating enzymatic activities, which is eliminate.

In view of the above, it is apparent that the cited art does not disclose recovery of microbially produced chymosin from a fermentation beer using a two phase liquid-liquid extraction method having partition coefficients for chymosin of greater than about 85.

It is further apparent that the cited art does not disclose the selective recovery of chymosin from a fermentation beer containing fermentation enzymes in addition to chymosin, i.e., most of the chymosin is recovered in one layer whereas most of the other fermentation enzymes are recovered in the other layer.

On the other hand, industrial or commercial scale production of chymosin by microbial activity and its subsequent purification is greatly facilitated by large partition coefficients for chymosin in a liquid-liquid two phase system and also by the selective recovery of chymosin from other fermentation enzymes contained in the beer when such two phase systems are employed.

Accordingly, it is an object of this invention to provide efficient processes for the recovery of microbially produced chymosin from aqueous mixtures of enzymes produced by fermentation or other microbial activity and particularly for commercial scale production of chymosin.

It is a further object of this invention to provide a recovery process for microbially produced chymosin using a liquid-liquid two phase system having partition coefficients for chymosin of greater than about 85.

It is still a further object of this invention to provide a recovery process for microbially produced chymosin using a liquid-liquid two phase system which provides for the selective recovery of chymosin from other polypeptides contained in the fermentation beer including other enzymes.

It is a further object of this invention to provide a process for the recovery and purification of microbially produced chymosin.

These and other objects are achieved by the present invention as evidenced by the attached summary of the invention, detailed description of the invention, examples, and claims.

SUMMARY OF THE INVENTION

In one aspect, this invention is a method for recovering microbially produced chymosin from an aqueous fermentation beer additionally containing fermentation polypeptides which comprises adding to the fermentation beer an effective amount of polyethylene glycol (PEG) and an inorganic salt so as to form a two phase system, allowing the fermentation beer-polyethylene glycol-inorganic salt mixture to separate into a chymosin-rich, fermentation polypeptide-poor polymer phase and a chymosin-poor, fermentation polypeptide-rich salt phase, and recovering the chymosin-rich, fermentation polypeptide-poor polymer phase.

Surprisingly, this recovery method provides for selective recovery of chymosin from the fermentation polypeptides found in the fermentation beer and also provides for partition coefficients for chymosin recovery which are greater than about 85 and preferably greater than about 100.

In general, the pH of the fermentation beer can be any pH at which the chymosin is stable, i.e., about 6.5 or less. However, in a preferred embodiment, it has been found that the use of lower pHs, i.e., pH 3 or less and preferably from about pH 2 to about 2.5, in the fermentation beer result in higher partition coefficients (higher selectivity) for the separation of chymosin into the polyethylene glycol phase, as high as 1000 or more, as compared to the use of pHs of from above 3 to about 6.5.

Accordingly, a preferred method aspect of the present invention relates to a method for recovering microbially produced chymosin from an aqueous fermentation beer additionally containing fermentation polypeptides which comprises adjusting the pH of the fermentation beer to less than about 3, then adding to the fermentation beer an effective amount of polyethylene glycol (PEG) and an inorganic salt so as to form a two phase system, allowing the fermentation beer-polyethylene glycol-inorganic salt mixture to separate into a chymosin-rich, fermentation polypeptide-poor polymer phase and a chymosin-poor, fermentation polypeptide-rich salt phase, and recovering the chymosin-rich, fermentation polypeptide-poor polymer phase.

In a further aspect of this invention, it has been found that chymosin can be separated from the polyethylene glycol phase by contacting the polyethylene glycol phase with an ion exchange resin under conditions wherein the chymosin binds to the resin. Under these conditions, the polyethylene glycol passes through the resin and chymosin is then recovered from the resin. Accordingly, this method aspect of the present invention relates to a method for recovering and purifying microbially produced chymosin from an aqueous fermentation beer additionally containing fermentation polypeptides which comprises a) adding to the fermentation beer an effective amount of polyethylene glycol (PEG) and an inorganic salt so as to form a two phase system, b) allowing the fermentation beer-polyethylene glycol-inorganic salt mixture to separate into a chymosin-rich, fermentation polypeptide-poor polyethylene glycol phase and a chymosin-poor, fermentation polypeptide-rich salt phase, c) recovering the chymosin-rich, fermentation polypeptide-poor polyethylene glycol phase, d) contacting the chymosin-rich, fermentation polypeptide-poor polyethylene glycol phase with an ion exchange resin under conditions wherein the chymosin binds to the resin and the polyethylene glycol passes through the resin; and e) recovering the chymosin from the resin.

In this aspect of the invention and for the reasons noted above, it is preferred that the pH of the initial fermentation beer be adjusted to about 3 or below before adding the polyethylene glycol/salt to the beer. It is also preferred that the pH remain below about 3 through the separation of the PEG phase and the contacting of the PEG phase with the ion exchange resin.

DETAILED DESCRIPTION OF THE INVENTION

The separation of various enzymes from aqueous solutions using polymers such as polyethylene glycol of various molecular weights in combination with other polymers, e.g., dextran, or inorganic salts is known in the art. However, this invention is directed in part to the unexpected discovery that extremely high partition coefficients for the extraction of microbially produced chymosin, particularly extracellularly produced chymosin, can be achieved by adding a sufficient amount of both polyethylene glycol and an inorganic salt to the fermentation beer so as to form a two phase system. Under these circumstances, almost all of the chymosin is partitioned into the polyethylene glycol phase. This is evidenced by partition coefficients for chymosin in the polyethylene glycol phase of greater than about 85 and preferably greater than about 100.

Further, this invention is also directed to the unexpected discovery that extraction (recovery) from the fermentation beer by the addition of polyethylene glycol and an inorganic salt is highly selective for microbially produced chymosin. That is to say that this extraction process is selective for chymosin and that other polypeptides (including other enzymes) found in the fermentation beer are preferentially retained in the chymosin-poor salt phase. This latter discovery is particularly surprising in view of the fact that the art which discusses enzyme recovery from an aqueous solution via the addition of a polymer and an inorganic salt does not teach selective recovery of one enzyme from other enzymes present in the solution.

However, prior to discussing this invention in detail, the following terms will first be defined:

"Microbially produced chymosin"—means a microbially produced polypeptide containing a sufficient homology of amino acids to naturally occurring chymosin as to possess the enzymatic activity of naturally occurring chymosin and having the partition characteristics of naturally occurring chymosin in the liquid-liquid two phase aqueous system described herein. Microbially produced chymosin is generally prepared by cultivating (fermenting) a host microorganism, i.e., a filamentous fungus, a bacteria, a yeast, and the like, transformed with a recombinant DNA sequence encoding all or a sufficient portion of chymosin so that the produced polypeptide possesses the enzymatic activity of naturally occurring chymosin. See, for example, U.S. Ser. No. 163,219 as well as U.S. Pat. No. 4,666,847 for disclosure of suitable transformed host microorganisms capable of generating microbially produced chymosin.

Microbially produced chymosin can be further classified as either intracellularly or extracellularly produced. Specifically, an intracellularly produced enzyme is one which is produced and retained in the host cell during fermentation and the completion of fermentation must be released from the cell, generally by lysing the cell. Cells can be conventionally killed and lysed by using heat. See, for instance, Wegner et al., U.S. Pat. No. 4,601,986. Another method useful on certain microorganisms is to change the osmotic pressure which causes the cells to lyse. See, for instance, Aubert et al., U.S. Pat. No. 4,299,858. Another conventional method used for lysing cells is by introduction of enzymes which break down the cell walls or membranes. Examples of this method are disclosed by Sugiyama, U.S. Pat. No. 3,816,260; Kobayashi et al, U.S. Pat. No. 3,890,198; and Kitamura et al., U.S. Pat. No. 3,917,510. The disclosures of the above patents are incorporated herein by reference.

An extracellularly produced enzyme is one which the microorganism is capable of transporting across the cell wall and accordingly, is found in the fermentation beer at the completion of the fermentation without any further treatment to the cells.

"Naturally produced chymosin"—refers to chymosin recovered from mammalian sources, including the fourth stomach of a calf.

"Fermentation beer"—refers to the chymosin containing solution recovered from the fermentation of the transformed host cell (microorganism) including any subsequent treatments which are performed on the beer. Such optional treatment steps include, for example, the killing of the cells (microorganisms) in the fermentation beer prior to addition of the inorganic salt and polyethylene glycol to the fermentation beer. Killing of the microorganism is preferably accomplished in the manner described in U.S. Ser. No. 07/365,945, which is incorporated herein by reference. Additionally, in some cases, it may be desireable to remove the cells and/or cell debris from the fermentation beer prior to addition of the inorganic salt and polyethylene glycol. Such removal can be effected by a filtration step which removes most or all of the solids including the cells and/or cell debris. Likewise, in some cases, it may be desirable to adjust the pH of the beer prior to addition the inorganic salt and polyethylene glycol. Also, for intracellularly produced chymosin, it is common to remove the lysed cells and recover inclusion bodies which contain the bulk of the chymosin which after refolding, is then treated in the manner of this invention.

"Fermentation polypeptides"—refer to the polypeptides, other than chymosin, which may be produced by the host microorganism during fermentation and which, in addition to chymosin, are contained in the fermentation beer at the time of addition of the polyethylene glycol and the inorganic salt. A major component of such fermentation polypeptides are enzymes which are co-produced during the fermentation. For example, the extracellular production of chymosin in the manner described in U.S. Ser. No. 07/163,219 also results in the production of enzymes such as alpha-amylase, acid phosphatase, leu amino peptidase, etc. which accordingly are found in the fermentation beer at the completion of fermentation. Likewise, when chymosin is produced intracellularly, enzymes in addition to chymosin may include any extracellular enzymes produced during fermentation of the host cells as well as the intracellular enzymes released upon lysis of the host cells at the completion of fermentation so as to release chymosin.

"Fermentation by-products"—refer to the non-polypeptide products contained in the fermentation beer at the time the polyethylene glycol and inorganic salt are added to the fermentation beer, including, for example, organic acids, complex carbohydrates, etc.

"Polyethylene glycol"—refers to any molecular weight polyethylene glycol which can be used to extract chymosin in the manner of this invention. Polyethylene glycol is available in molecular weights ranging from about 400 to about 22,000. Preferred polyethylene glycol for use herein should have a molecular weight in the range from about 600 to about 12,000. A particularly preferred polyethylene glycol is PEG-8000, i.e., polyethylene glycol having a molecular weight in the range of about 8,000. The selection of the polyethylene glycol used will depend in part on the composition of the mixture from which the chymosin is to be extracted and in part on economics of the process, as well as other factors.

"Inorganic salt"—refers to any inorganic salt which can be used to extract chymosin in the manner of this invention. Suitable inorganic slats include for instance, sulfate slats, phosphate salts, and the like. The sulfate salts are preferred including sodium sulfate, magnesium sulfate, ammonium sulfate, and the like. Additionally, mixtures of suitable salts can also be used as well as mixtures of such salts in combination with salt(s) such as sodium chloride, which by itself does not partition into a two phase system with polyethylene glycol but in combination with a suitable inorganic salt are known to enhance the partition coefficients of enzymes.

"Partition coefficient (K)"—is defined by the formula $$K = C_t/C_b$$

where $C_t$ refers to the equilibrium concentration of the partitioned compound in the top phase and $C_b$ refers to the equilibrium concentration of the partitioned compound in the bottom phase. Accordingly, it is apparent that the quantitative amount of partitioned compound in either phase depends on its partition coefficient as well as the volume of the phases. That is to say that if the partitioned compound has a partition coefficient of unity (the compound is equally partitioned in the top and bottom phases), then the phases will contain equal quantities of the partitioned compound only if the phases are of equal volume. If the top phase as 10% of the volume of the bottom phase, then when the partition coefficient is unity, the top phase will contain only 10% of the partitioned compound. In view of the above, it is further apparent that a very high partition coefficient for the partitioned compound is extremely valuable because it allows recovery of large quantities of this compound in the upper phase even when the volume of the upper phase is relatively small as compared to the bottom phase. Thus, in the present invention, very high partition coefficients allow for the use of smaller quantities of polyethylene glycol while still achieving very high recoveries of chymosin.

"Isoelectric point (IP)"—refers to the pH at which a polypeptide will be electrostatically neutral, i.e., the polypeptide carries an equal number of positive and negative charged functionalities. The isoelectric point for chymosin is about 4.6. At a pH below its isoelectric point, chymosin will have a net positive charge; and at a pH above its isoelectric point, chymosin will have a net negative charge.

"Ion exchange resin"—refers to a protein compatible resinous material which is capable of electrostatically binding charged compounds. Ion exchange resins are well known in the art and include both cation and anion exchange resins.

In the practice of this invention, a solution of chymosin is contacted with an ion exchange resin under conditions wherein the chymosin will bind to the resin. Whether a cation or an anion exchange resin is employed in the present invention depends on the pH of the polyethylene glycol phase, i.e., whether the pH of the solution is above or below the isoelectric point of chymosin. Accordingly, contacting a solution containing chymosin with an ion exchange resin under conditions wherein the chymosin binds to the resin merely refers to adjusting the pH of the solution above or below its isoelectric point so that the chymosin binds to the resin employed.

The pH of the solution is generally about 6.5 or less, although pH's around the isoelectric point, i.e., pH from about 3.6 to about 5.0, are not preferred due to the low net electrostatic charge of chymosin which reduces its effectiveness in binding to the resin.

Additionally, when the polyethylene glycol phase (solution) is maintained at pH 3.0–5.0, the chymosin undergoes more efficient autolysis, although autolysis is appreciable slower in the polyethylene glycol solution than in water. In any event, maintaining the aqueous polyethylene glycol phase at between 3.0–5.0 will result in some losses in chymosin yield due to autolysis. Accordingly, when a cation exchange resin is employed, it is preferred that the pH of the solution be maintained below about 3.0; whereas when an anion exchange resin is employed, it is preferred that the pH be maintained at above about 5.0.

Preferably, for the reasons noted above, the pH of the polyethylene glycol solution is about 3 or less, preferably less than about 3, and more preferably, from about 2 to about 2.5. When low pH's are employed, it has been further found that the fermentation by-products are readily passed through the resin whereas at higher pH's (5 and above) and when using an anion exchange resin, some of the fermentation by-produces irreversibly bind to the anion exchange resin, thus shortening its useful life.

Preferred cation exchange resins for use in this invention include, for instance, IBF SP Spherodex, Pharmacia SP-Sephadex, Indion SP-2, IBF SP-Trisacryl, and the like. Preferred anion exchange resins for use in this invention include, for instance, IBF Q Spherodex, Pharmacia Q-Sephadex, Indion Q-2, IBF Q-Trisacryl, and the like.

The processes of this invention are useful for recovery and/or purification of microbially produced chymosin. When recovering and purifying microbially produced chymosin, the entire fermentation beer or mixture may be used in its crude form or, if desired, the fermentation mixture can first be filtered to remove most or all of the solids then the liquid filtrate used in the processes of this invention.

In one aspect of this invention, microbially produced chymosin is recovered by adding to the fermentation beer an effective amount of polyethylene glycol (PEG) and an effective amount of an inorganic salt so as to form a two phase system. The resulting solution is allowed to stand so as to separate into a chymosin-rich, fermentation polypeptide-poor polyethylene glycol phase and a chymosin-poor, fermentation polypeptide-rich salt phase. The chymosin-rich, fermentation polypeptide-poor polyethylene glycol phase is then recovered by conventional techniques.

It has been found that under these conditions, partition coefficients for chymosin in the polyethylene glycol phase of greater than 85 and preferably greater than 100 are achieved. While polyethylene glycol extraction is useful for recovering chymosin at higher pH levels, i.e., pH 6.5 or less, it is more efficient as when the process is conducted at a pH less than about 3. At such lower pHs, partition coefficients of up to 1000 or more can be achieved. High partition coefficients are particularly advantageous because such permit the use of smaller quantities of polyethylene glycol to achieve the desired separation of chymosin from the fermentation beer which, in turn, facilitates the later separation of chymosin from the polyethylene glycol, i.e., there is less polyethylene glycol to separate.

It has further been found that as a result of a single extraction, the polyethylene glycol phase can contain as much as 95% or more of the total chymosin initially present in the fermentation beer and contains very little, if any, fermentation polypeptides or fermentation by-products from the beer. Thus, in addition to providing a means for recovering substantially al of the microbially produced chymosin contained in the fermentation bee, this aspect of the present invention also provides for the selective recovery of chymosin from the beer. This selectivity for chymosin recovery allows for both chymosin recovery from the fermentation beer as well as separation of the chymosin from most of the fermentation polypeptides and fermentation by-products co-produced in the fermentation. Thus, recovery of chymosin in the manner of this invention will result in a polyethylene glycol phase having a contamination of chymosin by such fermentation polypeptides and fermentation by-products of at least about 75% less, and preferably at least about 90% less, as compared to the contamination of chymosin by such fermentation polypeptides and fermentation by-products prior to extraction, i.e., in the fermentation beer.

In another aspect of this invention, the polyethylene glycol phase containing the extracted chymosin is separated from the other phase or phases and the polyethylene glycol phase is contacted with an ion exchange resin while maintaining or adjusting the pH so that the chymosin will bind to the resin. Because the polyethylene glycol is not charged, under these conditions, it passes through the resin thus effecting purification of chymosin from the polyethylene glycol. Thus, when the isolated polyethylene glycol phase containing the extracted chymosin is contacted with the ion exchange resin under conditions where the chymosin binds to the resin, essentially all the chymosin comes out of the polyethylene glycol and is bound to the ion exchange resin and the polyethylene glycol pass through the resin column. After the initial contact, the resin is washed with either water or water and salt, preferably so not to remove the chymosin from the resin, to remove the remaining polyethylene glycol. Then the chymosin is eluted from the column using a salt solution and a buffer maintained at a pH which will remove the chymosin from the resin. Because of the high selectivity for chymosin recovery, it is unnecessary to use a gradient or step-wise elution of the resin because essentially the only enzyme or material which is bound by the resin from the polyethylene glycol phase and subsequently released from the resin is chymosin. Therefore, the chymosin can be eluted in one bulk step using the salt solution and raising or lowering the pH (depending of course, on whether a cation or anion exchange resin is employed) to cause the entire chymrosin content bound to the resin to be eluted in one batch. Preferably, a salt is added to the eluting solution to aid in the rate or degree of elution, or in some cases, i.e., with an anion exchange resin, to effect elution of the chymosin from the resin. Salts are preferably employed with the eluting solution since chymosin is usually sold in commercial form in a salt solution and accordingly, it is convenient to incorporate the salt with the chymosin at this point.

Although higher pH levels can be used throughout the process (pHs up to about 6.5), the efficiency of the polyetheylene glycol/inorganic salt mixture in extracting the chymosin from the fermentation beer and therefore the efficiency of the process is not as high as when low pH is maintained throughout the extraction step. Therefore, it is preferred to use low pH and accordingly, a cation exchange resin to increase the efficiency of the overall process.

When the preferred aspects of the above invention are combined by conducting the polyethylene glycol extraction at a pH of about 3 or below and contacting the separated polyetheylene glycol phase with a cation exchange resin while maintaining the low pH, it has been found that a single polyethylene glycol extraction and a single-pass contact with the ion exchange resin will recover in the range of 90 to 95% of the total chymosin present in the initial fermentation beer.

On the other hand, the use of a higher pH in the polyethylene glycol extraction step as well as an anion exchange resin while maintaining the pH above chymosin's isoelectric point also provides acceptable results, although in this embodiment, the resin life is diminished by the accumulation of irreversibly bound fermentation by-products. When a higher pH is employed to extract the chymosin, this latter problem can be avoided simply by adjusting the pH of the polyethylene glycol extract to below chymosin's isoelectric point and preferably, to about pH 3.6 or below and more preferably about pH 3 or below, and then contacting the chymosin with a cation exchange resin.

In addition to the high efficiency for chymosin recovery by using the polyethylene glycol/inorganic salt mixture herein described, it has been further found that the solubility of chymosin in polyethylene glycol is apparently so high that the chymosin moves from the aqueous phase into the polyethylene glycol phase very rapidly. The time required for extraction of the chymosin into the polyethylene glycol phase is usually so short that it is not a significant process design factor. This process is therefore very efficient and economic in operation and is easily scaled up for commercial production.

As is apparent and regardless of the pH employed, the herein described process involves moving the chymosin from the aqueous mixture into the more hydrophobic polyethylene glycol phase. This is driven, at least in part, by the salt concentration in the non-polyethylene glycol phase or phases. If a low molecular weight polyethylene glycol is used, the polyethylene glycol phase is less hydrophobic and a higher salt concentration is necessary in the non-polyethylene glycol phase(s), which adds to the cost of operation. If a higher molecular weight more hydrophobic polyethylene glycol is used, less salt will be needed in the process, but the separation rate may be lower because of the high viscosity of the higher molecular weight polyethylene glycol. Thus, the process of this invention can be optimized for any particular operation by selecting the desired polyethylene glycol molecular weight, the salt concentration and other parameters which provide the desired economics. One objective is usually to minimize the time required to move the chymosin into the polyethylene glycol phase, but another objective is usually to minimize the amount of salt used to effect the transfer of essentially all of the chymosin into the polyethylene glycol phase. While the salt concentration in the non-polyethylene glycol phases can be 20% by weight or higher, usually less than about 15% is required with the appropriate polyethylene glycol. For example, with PEG-8000, about 10-13% sodium sulfate is adequate. On the other hand, the minimum inorganic salt concentration is dictated by the concentration of the salt necessary to form a 2 phase system with polyethylene glycol. However, in a preferred embodiment, the inorganic salt concentration is from about 8.5 to about 20 weight to volume percent based on the volume of the fermentation beer.

Also, preferably, the polyethylene glycol concentration employed herein is less than about 20, and more preferably less than about 15, weight to volume percent based on the volume of the fermentation beer. For economics and ease of later separation, as little polyethylene glycol as possible is most preferably employed.

The exact concentration of polyethylene glycol and inorganic salt employed herein can readily be determined by the skilled artisan.

After the chymosin is bound by the ion exchange resin, the polyethylene glycol phase may be recovered and reused by collecting the polyethylene glycol phase which is passed through the resin and either further treating it with chemicals, such as activated charcoal, to remove additional impruities or by directly adding it back to another batch of starting materials.

Similarly, the ion exchange resin can be regenerated for use with subsequent batches of polyethylene glycol containing chymosin by washing the ion exchange resin with a solution of water adjusted to the appropriate pH. For example, when a cation exchange resin is employed, it can be regenerated by washing it with a solution of water containing enough sulfuric acid to make the pH about 2.

The above aspects of this invention which enable the recycling of polyethylene glycol and the reuse of the ion exchange resins particularly lend the processes of this invention to efficient commercial and industrial operation for the purification of industrial quantities of chymosin, particularly microbially produced chymosin.

Having described the invention in general terms the invention can be better understood by reference to the following embodiments of the invention which are illustrated in the following examples. However the scope of this invention is to be determined by the appended claims, whereas the following examples are merely illustrative embodiments of particular ways in which the invention disclosed herein can be practiced.

EXAMPLES

Example 1

This example describes a chymosin recovery process using aqueous two phase polyethylene glycol extraction followed by contact with ion exchange resin to produce food grade chymosin. The chymosin is recovered from fermentation of an *Aspergillus Niger var. awamori*. The process is described in terms of 3000 1 fermenter and a broth harvest volume of about 2500 1. When the fermentation is complete, the broth is inactivated by pH adjustment to 2.0-2.5 with sulfuric acid and addition of acetic acid. (See U.S. patent application Ser. No. 07/365,945, filed Jun. 13, 1989 by Lawlis et al., incorporated herein by reference.) The inactivation conditions are held for 1 hour at the fermentation temperature and air flow. This inactivation achieves sufficient viable cell reduction for containment to be broken. After inactivation, the pH is maintained at 2.0-2.5. The inactivation will require about 125 kg of sulfuric acid and 25 kg of acetic acid.

The broth is extracted using a PEG 8000/sodium sulfate system at pH 2.0-2.5 by diluting 3x with water followed by the addition of 4% wt/vol PEG 8000 (75 kg) and 10.5% wt/vol anhydrous sodium sulfate. Upon mixing PEG/salt system with the broth, the chymosin is extracted into the PEG phase in a short period of time. The two phase mixture is separated using an extraction centrifuge. The chymosin-rich, PEG phase is collected for further processing. Using this process the 2500 1 of broth is diluted to about 7500 1 for the PEG extraction and yields about 700 1 of PEG phase extract.

The extract is diluted 3x with deionized water and filtered through cellulose pads before the ion exchange step. The filtered extract is passed through a 10 1 column of IBF Spherodex SP cation exchange resin having a particle size of 40-100 microns. The loaded column is washed with 30 1 of 6% NaCl solution of pH 2. The column is eluted with 2M NaCl and 50 mM phosphate buffer at pH 6.0. The capacity of the ion exchange resin is up to about 60 g chymosin per 1 of resin. The eluted fraction containing the chymosin is collected for further processing. The column is regenerated for reuse by washing with water adjusted to pH 2 with sulfuric acid. The eluted chymosin solution is made 17% NaCl for commercial food grade use, or can be processed for other purposes, if desired.

Example 2

This example illustrated the high partition of chymosin into the PEG phase obtained by the process of this invention. Using the same fermentation broth of Example 1 above, inactivated in the same way, the following extractions were performed on whole broth (Sample 1) and on a filtrate thereof from a rotary vacuum drum filter (Samples 2 and 3). All three samples were maintained at pH 2 for processing and were extracted with 5% PEG 8000 and 10% sodium sulfate wt/vol. Samples 1 and 2 were phase separated in a bottle centrifuge (RC3B) and Sample 3 was separated in an SA-1 continuous laboratory centrifuge.

| | VOL. (1) | ACT. (CHU/1) | TOTAL CHYMOSIN (CHU) | RECOVERY (%) |
|---|---|---|---|---|
| SAMPLE 1: EXTRACTION OF WHOLE BROTH | | | | |
| RAW FEED | 10 | 30 | 300 | |
| TREATED FEED | 15 | 13 | 195 | |
| PEG PHASE | 1.7 | 206 | 350 | 117 |
| REMAINDER | 13 | 1.5 | 19 | 5 |
| | | | MASS BAL = | 122 |
| | | | K = | 141 |
| SAMPLE 2: EXTRACTION OF FILTRATE | | | | |
| RAW FEED | 14 | 13.7 | 192 | |
| PEG PHASE | 3.3 | 49 | 164 | 85 |
| REMAINDER | 11.3 | 0.78 | 9 | 5 |
| | | | MASS BAL = | 90 |
| | | | K = | 62 |
| SAMPLE 3: EXTRACTION OF FILTRATE | | | | |
| RAW FEED | 430 | 7.16 | 3078 | |
| PEG PHASE | 62 | 52.3 | 3127 | 104 |
| REMAINDER | 385 | 0.24 | 96 | 3 |
| | | | MASS BAL = | 107 |
| | | | K = | 201 |

(CHU - Chris. Hansen Unit - 1 CHU/ml, under the following conditions: Substrate: 110 g of low heat, spraydried skim milk powder is suspended in 1000 ml 0.05% calcium chloride. The milk is stirred for 30 minutes at room temperature and then left for rest for another 30 minutes. The milk should be stored at a temperature between 4 and 25° C. and not longer than 3 hours. The pH of the milk is about 6.5. Temperature: 32° C. plus or minus 0.2° C. in a thermostatic water bath. Enzyme addition: To 25 ml of the reconstitute skim milk is added 0.5 ml of enzyme solution, diluted to give a clotting time between 380 and 500 seconds, and which will give a clotting time of 410 to 460 seconds)

The above mass balances are not 100% because the methods used for measurement of certain values are imprecise and provide approximate values. Nevertheless, the above tests illustrate the relative partitioning of the chymosin achieved by this invention allowing for the experimental error of the test methods.

Example 3

In this example of PEG phase similar to Example 1 diluted as indicated with deionized water and filtered was passed through a column of 1.0 ml of each resin, equilibrated in pH=2.0 deionized water. Flow rate was 1.0 ml/min, washed with pH=2.0 DI water. Eluted with pH=5.8, 2M NaCl, 50 mM sodium phosphate (pi).

| | | | RESIN: | | | | | |
|---|---|---|---|---|---|---|---|---|
| IBF SP-SPHERODEX DILUTION | | PHARMACIA SP-SEPHA. DILUTION | | INDION SP-2 DILUTION | | IBF SP-TRISACRYL DILUTION | | |
| 1:2 | 1:4 | 1:2 | 1:4 | 1:2 | 1:4 | 1:2 | 1:4 | |
| | | | LOADED (mgs) | | | | | |
| 34.3 | 34.3 | 34.3 | 34.3 | 34.3 | 34.3 | 34.3 | 17.6 | |
| | | | UNBOUND (mgs) | | | | | |
| 9.8 | 3.82 | 26.5 | 0.312 | 34.8 | 17.6 | 27.3 | 0.338 | |
| | | | ELUTED (mgs) | | | | | |
| 26.5 | 26 | 8.84 | 21.2 | 0.32 | 1.05 | 10.8 | 17.3 | |
| | | | MASS BAL. (%) | | | | | |
| 106 | 87 | 103 | 63 | 102 | 54 | 111 | 100 | |

Example 4

This example is the same as Example 3 except the following was used for multiple elution: 670 mls SP-Spherodex Resin; load and elute @ 450 mls/min; load 1:4 dilution of PEG Extract pH=2.0; wash with DI H2O pH 2.0, 2M NaCl pH 2.0; elute with 2M NaCl, 200 mM Pi, pH 5.8.

| # | Desc. | Vol. (1) | CHU/l | CHU |
|---|---|---|---|---|
| 1 | START | 240 | 11.07 | 2656.8 |
| 2 | VOID 1 | 170 | 0.69 | 117.3 |
| 3 | VOID 2 | 60 | 7.21 | 432.6 |
| 4 | DI WASH | 2.5 | 0 | 0 |
| 5 | NaCl WASH | 7.4 | 4.89 | 36.186 |
| 6 | ELUT #1 | 1 | 1347 | 1347 |
| 7 | ELUT #2 | 1 | 924 | 924 |
| 8 | ELUT #3 | 1 | 214 | 214 |
| 9 | ELUT #4 | 1 | 108 | 108 |
| 10 | ELUT #5 | 1 | 25.6 | 25.6 |
| 11 | ELUT #6 | 1 | 13.8 | 13.8 |
| MASS BALANCE: | | | | 121.14 |
| YIELD (% OF BOUND): | | | | 127.13 |
| CAPACITY (MG/ML): | | | | 51.08 |

Example 5

This example is the same as Example 4 except 860 mls PEG extract were treated with 1% "Nuchar SA" charcoal for 30 minutes, filtered, then diluted 1:3 and fed to a column of 2.5 mls resin having a bed depth of 3.2 cm. The results were as follows:

| # | DESC. | VOL. (1) | Mg/l | gms |
|---|---|---|---|---|
| 1 | Start | 2,600 | 75 | 195 |
| 2 | Void | 2,600 | 22.5 | 58.5 |
| 3 | DI | 20 | 15.7 | 0.314 |
| 4 | Salt | 30 | 137 | 4.11 |
| 5 | Composite | 36 | 3,667 | 132.0 |
| | | | (280 CHU/ml) | |

Mass Balance: $\frac{194.9 \text{ g}}{195 \text{ g}} (100) = 99.9\%$

Yield of Bound: $\frac{132 \text{ g}}{136.5 \text{ g}} (100) = 96.7\%$

| # | DESC. | VOL. (1) | Mg/l | gms |
|---|---|---|---|---|

Capacity: $\frac{132 \text{ mgs}}{2.5 \text{ ml}} = 52.8 \text{ g/l}$

Example 6

In manner similar to the extraction procedure set forth in Example 2 above but using a pH of about 5.8, the enzymes listed below were extracted from an aqueous solution into the polyethylene glycol phase of the liquid-liquid 2 phase system to provide the following results (pure enzyme used):

| Enzyme | Protein (mg/ml) | Activity CHU/ml | Partition Coefficient |
|---|---|---|---|
| calf chymosin | 1.7 | 28 | 87 |
| bovine pepsin | 1.9 | 31 | 31.5 |
| porcine pepsin | 2.3 | 29.7 | 1.45 |
| E. parasitica aspartic protease | 3.6 | 27 | 0.33 |
| M. miehei aspartic protease | 2.4 | 20.5 | 0.24 |

This experiment was repeated but at this time at pH 2-2.5 with the following results:

| Enzyme | Protein (mg/ml) | Activity CHU/ml | Partition Coefficient |
|---|---|---|---|
| calf chymosin | 1.2 | 89 | >943 |
| bovine pepsin | 1.3 | 50 | >462 |
| porcine pepsin | 1.6 | 23.7 | >206 |
| E. parasitica aspartic protease | 2.5 | 15.2 | 1.18 |
| M. miehei aspartic protease | 1.7 | 48 | 0.94 |

The above results indicate that while chymosin provides excellent partition coefficients, i.e., above about 85 at either pH 5.8 or 2-2.5, bovine pepsin and porcine pepsin provide excellent partition coefficients only at the lower pH. However, neither bovine pepsin nor procine pepsin are polypeptides found in fermentation beer. On the other hand, the above data further indicates that microbial rennet, i.e., E. parasitica aspartic protease and M. miehei aspartic protease, do not possess significant partition coefficients at either the lower or the higher pH tested.

Example 7

The following example is a direct comparison of the partition coefficients at pH 2.5 and 5.5 for chymosin as well as for alpha-amylase, acid phosphate, leu amino peptidaseamylase, and glucoamylase (GAM), found in the fermentation beer of *Aspergillus Niger var. awamori*. The extraction was conducted in the manner of Example 2 above with the exceptions noted below:

| | Chymosin | |
|---|---|---|
| Sample | Starting Conc. CHU/ml | Partition Coefficient |
| pH 2.5 no cells[a] | 7 | 98 |
| pH 5.5 no cells | 5.9 | 92 |
| pH 2.5 with cells[b] | 6.3 | 96 |

Alpha Amylase (continued)

| Sample | Starting Conc. IU/ml | Partition Coefficient |
|---|---|---|
| pH 5.5 with cells[c] | 5.9 | 88 |

Alpha Amylase

| Sample | Starting Conc. IU/ml | Partition Coefficient |
|---|---|---|
| pH 2.5 no cells[a] | 19,400 | approaches 0 |
| pH 5.5 no cells[a] | 19,400 | approaches 0 |
| pH 2.5 with cells[b] | 19,400 | approaches 0 |
| pH 5.5 with cells[c] | 19,400 | approaches 0 |

GAM

| Sample | Starting[d] Conc. | Partition Coefficient |
|---|---|---|
| pH 2.5 no cells[a] | 3,777.5 | approaches 0 |
| pH 5.5 no cells[a] | 3,777.5 | 0.001451 |
| pH 2.5 with cells[b] | 3,777.5 | 0.001988 |
| pH 5.5 with cells[c] | 3,777.5 | 0.000980 |

Acid Phosphatase

| Sample | Starting Conc. IU/ml | Partition Coefficient |
|---|---|---|
| pH 2.5 no cells[a] | 594 | approaches 0 |
| pH 5.5 no cells[a] | 594 | approaches 0 |
| pH 2.5 with cells[b] | 594 | approaches 0 |
| pH 5.5 with cells[c] | 594 | approaches 0 | leu amino peptidase

| Sample | Starting Conc. U/ml | Partition Coefficient |
|---|---|---|
| pH 2.5 no cells[a] | 1,639 | approaches 0 |
| pH 5.5 no cells[a] | 1,639 | 0.000182 |
| pH 2.5 with cells[b] | 1,639 | approaches 0 |
| pH 5.5 with cells[c] | 1,639 | approaches 0 |

[a] fermentation beer centrifuged to remove cells without first killing the cells
[b] fermentation beer not centrifuged and cells are still alive
[c] fermentation beer not centrifuged and cells are still alive
[d] starting concentration reported in microgram glucose/ml/min. Starting conc. (all enzymes) were determined at pH 5.5.

The above data demonstrates that while chymosin is partitioned into the polyethylene glycol phase, the other enzymes in the fermentation beer are not. Thus, this data establishes that chymosin is selectively partitioned into the polyethylene glycol phase when in the presence of fermentation polypeptides.

Example 8

A one liter aliquot of *Aspergillus Niger var. awamori* at pH 5.8 was centrifuged to remove cells (not killed) on a RC-3B centrifuge (Sorvall) at appropriately 5000 x g for about 15 minutes. The resulting fermentation broth was warmed to about 37° C. To this solution was added sodium sulfate (10.5 wt to vol. percent) and PEG 8000 (4 wt. to vol. percent). The solution was mixed until the components dissolved. The solution was then subjected to centrifugation at 5000 x g (on the centrifuge) for about 15 minutes to enhance the separation of the resulting phases. The chymosin-rich polyethylene glycol phase (top phase) was separated from the salt-rich phase (bottom phase) by removing the bottom phase with a perstaltic pump. One-half of the top phase (45 ml) was diluted 1 to 3 with distilled water and loaded onto a 2.5 ml Pharmacia Q-sepharose column equilibrated with 50 mM sodium phosphate, pH 5.8. The column was washed with 14 column volumes of the same buffer. The chymosin was eluted with 50 mM sodium phosphate, pH 5.8, 2M NaCl. The volume of eluant was 45 ml. The results are as follows:

| | Vol. (in liters) | Act. (CHU/ml) | Total Chymosin | Percent Recov. |
|---|---|---|---|---|
| Raw Broth | 1 | 11.6 | 11,600 | 100 |
| Extract | 0.0925 | 102.9 | 9,775[e] | 84 |
| Raffinate | 0.925 | 0.53 | 490 | 4 |
| Q-seph. void | 0.101 | — | 154 | 3 |
| Q-seph. elute | 0.045 | 75 | 3,375 | 69[f] |
| Overall recovery | | | | 58 |
| Mass balance | | | | 69 |
| Partition Coefficient (K) | | | | about 190[g] |

[e] as noted above, only one-half of the extract was used which means that only one-half of the chymosin (9775/2 or 4887 CHU) was applied to the anion exchange resin.
[f] 69% recovery is the yield achieved in comparison to the amount of chymosin found in the extract.
[g] Partition coefficients of about 200 or more are difficult to measure accurately because of assay limitations. That is to say that because the partition coefficient is a ratio of the concentration of chymosin in the top phase divided by the concentration of the chymosin in the bottom phase and further because the amount of chymosin in the bottom phase is generally very small, small changes in this bottom concentration will produce large swings in the partition coefficient. Moreover, the concentration determined by assay methodology is particularly subject to variations at very low concentrations.

By following the procedures exemplified above, substantially pure chymosin is recovered. That is to say that the chymosin is at least about 90% by weight pure and preferably, at least about 95% by weight pure and can be prepared for commercial use without further significant treatment to remove impurities. The commercial chymosin product is usually diluted to about 5 grams per gallon or about 1.5 grams per liter chymosin. The salt (usually NaCl) concentration is normally brought up to about 18% and a preservative such as sodium benzoate is added. The final concentrated product intended for food grade use usually is also subjected to a final filtration to remove any undesirable solids or particles that may be present.

What is claimed is:

1. A method for recovering microbially produced chymosin from an aqueous fermentation beer of a genetically engineered microorganism which expresses fermentation polypeptides and which has been modified to express a polypeptide containing a sufficient homology of amino acids to mammalian chymosin so as to posses the enzymatic activity of mammalian chymosin and the partition characteristics of mammalian chymosin in liquid-liquid two phase system using a polyethylene glycol phase and an aqueous-salt phase which method comprises:
   adjusting the pH of the aqueous fermentation beer to less than about 6.5,
   adding to the fermentation beer an effective amount of polyethylene glycol and an inorganic salt so as to form a two phase system,
   allowing the fermentation beer-polyethylene glycol-inorganic salt mixture to separate into a chymosin-rich, fermentation polypeptide-poor polymer phase and a chymosin-poor, fermentation polypeptide-rich salt phase, and
   recovering the chymosin-rich, fermentation polypeptide-poor polymer phase.

2. A method according to claim 1 wherein the pH of the fermentation beer is about 3 or less.

3. A method according to claim 2 wherein the pH of the fermentation beer is less than about 2.8.

4. A method according to claim 1 wherein the average molecular weight of the polyethylene glycol is from about 600 to about 12,000.

5. A method according to claim 4 wherein the average molecular weight of the polyethylene glycol is from about 5,000 to about 10,000.

6. A method according to claim 1 wherein said inorganic salt is selected from the group consisting of sulfate salts and phosphate salts.

7. A method according to claim 6 wherein said inorganic salt is a sulfate salt.

8. A method according to claim 7 wherein said sulfate salt is selected from the group consisting of sodium sulfate, magnesium sulfate, and ammonium sulfate.

9. A method according to claim 1 wherein said aqueous fermentation beer is first filtered prior to addition of said polyethylene glycol and said inorganic salt.

10. A method for recovering microbially produced chymosin from an aqueous fermentation beer of a genetically engineered microorganism which expresses fermentation polypeptides and which has been modified to express a polypeptide containing a sufficient homology of amino acids to mammalian chymosin so as to possess the enzymatic activity of mammalian chymosin and the partition characteristics of mammalian chymosin in liquid-liquid two phase systems using a polyethylene glycol phase and an aqueous-salt phase which method comprises:

adjusting the pH of the aqueous fermentation beer to less than about 3, adding to the fermentation beer an effective amount of polyethylene glycol and an inorganic salt so as to form a two phase system, allowing the fermentation beer-polyethylene glycol-inorganic salt mixture to separate into a chymosin-rich, fermentation polypeptide-poor polymer phase and a chymosin-poor, fermentation polypeptide-rich salt phase, and recovering the chymosin-rich, fermentation polypeptide-poor polymer phase.

11. A method according to claim 10 wherein the average molecular weight of the polyethylene glycol is from about 600 to about 12,000.

12. A method according to claim 11 wherein the average molecular weight of the polyethylene glycol is from about 5,000 to about 10,000.

13. A method according to claim 10 wherein said inorganic salt is selected from the group consisting of sulfate salts and phosphate salts.

14. A method according to claim 13 wherein said inorganic salt is a sulfate salt.

15. A method according to claim 14 wherein said sulfate salt is selected from the group consisting of sodium sulfate, magnesium sulfate, and ammonium sulfate.

16. A method according to claim 10 wherein said aqueous fermentation beer is first filtered prior to addition of said polyethylene glycol and said inorganic salt.

17. A method for recovering and purifying microbially produced chymosin from an aqueous fermentation beer of a genetically engineered microorganism which expresses fermentation polypeptides and which has been modified to express a polypeptide containing a sufficient homology of amino acids to mammalian chymosin and the partition characteristics of mammalian chymosin in liquid-liquid two phase systems using a polyethylene glycol phase and an aqueous-salt phase which method comprises:

adjusting the pH of the aqueous fermentation beer to less than about 6.5, adding to the aqueous fermentation beer an effective amount of polyethylene glycol and an inorganic salt so as to form a two phase system, allowing the fermentation beer-polyethylene glycol-inorganic salt mixture to separate into a chymosin-rich, fermentation polypeptide-poor polyethylene glycol phase and a chymosin-poor, fermentation polypeptide-rich salt phase, recovering the chymosin-rich, fermentation polypeptide-polyethylene glycol phase, contacting the chymosin-rich, fermentation polypeptide-poor polyethylene glycol phase with an ion exchange resin under conditions wherein the chymosin binds to the resin and the polyethylene glycol passes through the resin; and recovering the chymosin from the resin.

18. A method according to claim 17 wherein the average molecular weight of the polyethylene glycol is from about 600 to about 12,000.

19. A method according to claim 18 wherein the average molecular weight of the polyethylene glycol is from about 5,000 to about 10,000.

20. A method according to claim 17 wherein said inorganic salt is selected from the group consisting of sulfate salts and phosphate salts.

21. A method according to claim 20 wherein said inorganic salt is a sulfate salt.

22. A method according to claim 21, wherein said sulfate salt is selected from the group consisting of sodium sulfate, magnesium sulfate, and ammonium sulfate.

23. A method according to claim 17 wherein said aqueous fermentation beer is first filtered prior to addition of said polyethylene glycol and said inorganic salt.

24. A method according to claim 25 wherein the pH of the fermentation beer is about 3 or less.

25. A method according to claim 24 wherein the pH of the fermentation beer is less than about 2.8.

26. A method according to claim 17 wherein the pH of said chymosin-rich, fermentation polypeptide-poor polyethylene glycol phase is either from 5.0 to 6.5 or is about 3.0 or less.

27. A method according to claim 26 wherein the pH of said chymosin-rich, fermentation polypeptide-poor polyethylene glycol phase is about 3.0 or less and a cation exchange resin is employed.

28. A method according to claim 26 wherein the pH of said chymosin-rich, fermentation polypeptide-poor polyethylene glycol phase is from about 5.0 to about 6.5 and an anion exchange resin is employed.

29. A method according to claim 17 wherein the polyethylene glycol and inorganic salt are added at a pH of about 3 or less and after isolation of the chymosin-rich, fermentation polypeptide-poor polyethylene glycol phase, the pH of this phase is adjust to from about 5.0 to 6.5 and an anion exchange resin is employed.

* * * * *

UNITED STATES PATENT AND TRADEMARK OFFICE
CERTIFICATE OF CORRECTION

PATENT NO. : 5,139,943  
DATED : August 18, 1992  
INVENTOR(S) : Henry G. Heinsohn et al.

Page 1 of 3

It is certified that error appears in the above-indentified patent and that said Letters Patent is hereby corrected as shown below:

Col. 1, line 43, "be" should read —by—
Column 1, line 44, where "E. coli" should read --E. coli--;
        Line 46, where "be" should read --by--;
        line 47, where "Saccharomyces cerevisiae" should read --Saccharomyces cerevisiae--; and
        line 55, where "phosphates" should read --phosphatase--;

Column 3, line 7, where "eliminate" should read --eliminated--;

Column 4, line 45, where "d)" should begin a new paragraph;

Column 6, line 21, where --of-- should be inserted after the word "addition";
        line 67, where "slats" should read --salts--; and
        line 68, where "slats" should read --salts--;

Column 8, line 18, where "by-produces" should read --by-products--;
        line 53, where "as" should be deleted;

Column 9, line 1, where "al" should read --all--;
        line 2, where "bee" should read --beer--; and
        line 34, where --as-- should be inserted after "so";

Column 11, line 44, where "Niger" should read --niger--;

Column 12, line 19, where "illustrated" should read --illustrates--;

Column 13, line 3, where "of" should read --a--;

UNITED STATES PATENT AND TRADEMARK OFFICE
CERTIFICATE OF CORRECTION

PATENT NO. : 5,139,943
DATED : August 18, 1992
INVENTOR(S) : Henry G. Heinsohn et al.

It is certified that error appears in the above-indentified patent and that said Letters Patent is hereby corrected as shown below:

Column 14, line 23, where "E. parasitica" should read --<u>E. parasitica</u>--;

line 25, where "M. miehei" should read --<u>M. miehei</u>--;
line 37, where "E. parasitica" should read --<u>E. parasitica</u>--;
line 39, where "M. miehei" should read --<u>M. miehei</u>--;
line 49, where "E. parasitica" should read --<u>E. parasitica</u>--;
line 50, where "M. miehei" should read --<u>M. miehei</u>--;
line 57, where "phosphate" should read --phosphatase--; and
line 59, where "<u>Niger</u>" should read --<u>niger</u>--;

Column 15, line 43, where "<u>Niger</u>" should read --<u>niger</u>--;

Column 16, line 44, where "posses" should read --possess--;

Column 17, line 61, where --so as to possess the enzymatic activity of mammalian chymosin-- should be inserted after "chymosin" and

UNITED STATES PATENT AND TRADEMARK OFFICE
CERTIFICATE OF CORRECTION

PATENT NO. : 5,139,943
DATED : August 18, 1992
INVENTOR(S) : Henry G. Heinsohn et al.

It is certified that error appears in the above-indentified patent and that said Letters Patent is hereby corrected as shown below:

Column 18, lines 13 and 14, where "polypeptide-polyethylene"
should read --polypeptide-poor polyethylene--;
line 39, where "25" should read --17--; and
line 59, where "adjust" should read --adjusted--.

Signed and Sealed this

Tenth Day of January, 1995

Attest:

BRUCE LEHMAN

Attesting Officer

Commissioner of Patents and Trademarks